United States Patent [19]

Barthelemy et al.

[11] Patent Number: 4,588,594
[45] Date of Patent: May 13, 1986

[54] PROCESS FOR PREPARING IMPROVED QUALITY CHEESES AND PRODUCT PRODUCED

[75] Inventors: Pierre Barthelemy, Barbery; Jean Lablee, Mamirolle, both of France

[73] Assignee: Roussel Uclaf, Paris, France

[21] Appl. No.: 489,454

[22] Filed: Apr. 28, 1983

[30] Foreign Application Priority Data

Apr. 30, 1982 [FR] France .............................. 82 07483

[51] Int. Cl.⁴ .............................................. A23C 9/12
[52] U.S. Cl. ...................................... 426/36; 426/40; 426/42
[58] Field of Search ....................... 426/36, 38, 40, 42

[56] References Cited

PUBLICATIONS

Desmazeaud et al.,–Chem. Abst., vol. 70, (1969), p. 111743j.

*Primary Examiner*—Sam Rosen
*Attorney, Agent, or Firm*—Bierman, Peroff & Muserlian

[57] ABSTRACT

A process for improving the cheese capacity of milk used in the preparation of soft paste cheeses intended to be ripened comprising adding during the course of the preparation of the soft paste cheese an enzyme extracted from a culture of *Micrococcus caseolyticus* to the milk; and the cheese prepared thereby.

9 Claims, No Drawings

PROCESS FOR PREPARING IMPROVED QUALITY CHEESES AND PRODUCT PRODUCED

STATE OF THE ART

The present invention relates to a process for improving the cheese capacity of milk used in the preparation of soft paste cheeses intended to be ripened; as well as the cheese obtained by this process.

It is known that the techniques followed in collecting milk, preserving it at the farm, transporting it by tank truck and holding it at the creamery in tanks have the gravest consequences on the bacterial flora whose activity is essential for the production of a quality cheese. The holding of milk at 4° C. particularly has an effect on the selection of psychrotrophic bacteria which produce the amino acids harmful to the quality of the cheese. This selection is made to the detriment of the lactic bacteria which secrete, during the course of ripening, the necessary enzymes required for obtaining a cheese of good quality.

The production of soft past cheese is described, for example, in U.S. Pat. Nos. 2,793,122, 3,156,568 and 4,158,607; as well as in Swiss Pat. No. 345,318 and Moreno et al, J. of Dairy Sci. 56 no1 p33–38(1973). In this production starter cultures are employed such as those from *Micrococcus caseolyticus*.

OBJECTS OF THE INVENTION

An object of the present invention is to determine how to recover the cheese capacity of milk comparable to that which existed in former times.

Another object of the present invention is the development of a process for improving the cheese capacity of milk used in the preparation of soft paste cheeses intended to be ripened comprising adding during the course of the preparation of the soft paste cheese an enzyme extracted from a culture of *Micrococcus caseolyticus* to the milk; and the cheese prepared thereby.

These and other objects of the invention will become more apparent as the description thereof proceeds.

DESCRIPTION OF THE INVENTION

During the course of research to determine how to recover the cheese capacity of milk, the applicant unexpectedly found that the addition of an enzyme extracted from a culture of *Micrococcus caselyticus* considerably improved the cheese capacity of milk used in the preparation of soft paste cheeses intended to be ripened.

While it is known from Chem. Abst. 70 (1969), p. 23 111743j that enzymes extracted from a culture of *Micrococcus caseolyticus* could be employed in the manufacture of cooked pressed paste cheeses, the use of the enzymes in production of soft paste cheeses would not have been anticipated.

The addition to the milk of enzymes extracted from a culture of *Micrococcus caseolyticus* answers particularly well the problems posed in non-uniform handling of the milk. On the one hand it acts to prepare the action of rennet in improving the capacity of coagulation of the milk and on the other hand it acts to create, by splitting of the casein, some peptides stimulating the lactic bacteria.

Because of this enzyme addition, the cheese maker can recover a milk having a traditional cheese making capacity by a reconstruction of its biological maturation processes.

According to the invention, the soft paste cheese is particularly a cheese having a moldycrust and having a dried extract weight of 30% to 50% of the soft paste cheese weight. Such cheeses are particularly Carré de l'Est, Camembert and Brie.

In conducting the process of the invention, all *Micrococcus caseolyticus* strains can be employed. However, the strain deposited in the Collection Nationale de Cultures de Microorganismes (C.N.C.M.) of the Pasteur Institute in Paris under No. I. 194 on Apr. 28, 1982, has been found to be particularly advantageous. This strain is indentical to the strain deposited in the collection of C.N.R.Z. (Centre National de Recherches Zootechniques at Jouy-en-Josas, France) under No. 467, which has in addition already been described in the literature.

The process of the invention is advantageously characterized in that the *Micrococcus caseolyticus* strain employed is that deposited at the Pasteur Institute of Paris, France under No. I. 194.

According to the invention, the addition of enzymes in the preparation of soft paste cheeses causes acceleration and regularization of the proteolysis while shortening the period of ripening. This enzyme addition, which principally causes an advance of the possible period of commercialization of the cheese, has, in addition, the effect of prolonging commercialization beyond the usual duration. Thus, for example, for Carré de l'Est, where the normal period of commercialization starts toward the 25th day of ripening and is over by the 31st day, the commercialization can start toward the 21st day of ripening and can terminated about the 39th day of ripening.

It should however be noted that the amount of enzyme dosed has a prime importance in the operation of the invention. If a too weak dosage is employed, it is found to be without action, whereas a too large dosage causes a very rapid maturation of the cheese which thus gives extreme fluidity and the cheese cannot be commercialized.

The process of the invention is thus characterized in that the enzyme additions is made at a dosage of between 50 and 190 U per liter of milk. Preferentially, the enzyme addition is made at a dosage of between 70 and 150 U per liter of milk. The enzyme increases the capacity of coagulation of the milk and the optimum dosage is that which shortens the time on the order of from 1 to 5 minutes. This dosage, which varies as a function of the quality of the milk and of cheeses to be prepared, is situated most often in the neighborhood of 100 U/liter.

The proteolytic activity of the enzyme is determined by measurement (variation of the optical density at 275 nm) of the amount of casein hydrolysed by the enzyme (unprecipitable by trichloroacetic acid) under standard conditions.

One unit (U) is defined as the amount of enzyme which acting under the conditions of the dosage, causes a variation of the optical density at 275 nm of 0,001 unit of optical density per minute per milliliter of solution.

According to the process of the invention, the addition of the enzyme is made before or during the rennet treatment. This enzyme addition is preferably made some 15 to 20 minutes before the rennet treatment under the condition where the milk temperature is equal or greater than 35° C. In the case where the temperature of the rennet treatment is only in the order of 30° to 32° C., the temperature least favorable to the activity of the enzyme, this must be introduced at least 40 minutes before the rennet treatment.

In the case where the technique of cheese making does not allow the maintaining of this preliminary contact time, the enzyme can be introduced in the milk prematuration tank starting from the eve of the day of cheese making (milk at a temperature generally between 10° and 16° C.), or in the storage tank (milk at 4° C.) when the technique of prematuration is not utilized.

Another technique can be applied in the case where the milk of these tanks has undergone a pasteurization (72° C.) or a thermization (63° C.) just before starting the cheese making. In order to avoid the partial or total destructions of the enzyme by heat, the technique consists in diluting the total quantity of enzyme, utilizing, for example, for this treatment, for a tank of 10,000 liters, from 700,000 to 1,500,000 units, in one liter of sterile milk, the day before the cheese making. This enzymatic predilution or preparation is kept at room temperature of about 20° C. The enzymatic preparation is next poured into the cheese making tank at the start of filling the same.

This technique consequently causes the total hydrolysis of the casein contained in the liter of milk, being about 26 gm, thus giving an equivalent amount of stimulating supplementary peptides reinforcing the normal action of the enzyme which remains intact in thus preparation.

According to a variant in the process of the invention, the enzyme addition is made during the course of stirring.

The technique of preparation of soft paste cheeses being known in itself, the following examples are given only to illustrate the addition of enzymes extracted from a culture of *Micrococcus caseolyticus.*

The invention also relates to the soft paste cheese obtained by the process described above.

It is pointed out that the process of the invention can be employed starting from entire natural milk as well as starting from reconstituted, recombined or ultrafiltered milk. The process of ultrafiltration is not without inconvience for the production of a quality cheese. While retaining all the proteins and mineral salts of which a part was previously lost with the serum, the ultrafiltration contributes in obtaining a cheese most difficult to ripen and in changing its organoleptic characteristics.

The addition of the enzymes extracted from a culture of *Micrococcus caseolyticus* allows the alleviation of these major inconveniences. For example, for a soft paste cheese having a moldy crust of the St. Marcelin type, the duration of ripening, which is normally some 24 days, can be reduced to 17 days with the obtention of a more mellow product.

The invention therefore also relates to the application of an enzyme extracted from a culture of *Micrococcus caseolyticus,* such as defined above to the preparation of soft paste cheeses intended to be ripened.

The enzyme extracted from a culture of *Micrococcus caseolyticus,* as used in the process of the invention, can be prepared, for example, according to the technique described in Ann. Biol. Anim. Bioch. Biophys. 8 (1968) 565–577 and 10 (1970) 413–430.

This extracted enzyme from *Micrococcus caseolyticus* can be prepared starting from a broth of the culture of *Micrococcus caseolyticus* by centrifugation of the said broth in order to eliminate the bacteria. The enzyme is then precipitated by ammonium sulfate. This precipitate is then taken up in a solution of calcium chloride and concentrated by ultrafiltration followed by a lyophilization.

This preparation is set out in the following:

PREPARATION OF THE FERMENTATION BROTH

A solution of 750 liters of water, 20 kg of corn steep liquor, 20 kg of casein peptone, 10 kg of yeast autolysate and 0,906 kg of calcium chloride was prepared in a fermenter and adjusted to a pH of 7 by addition of sodium hydroxide solution. The solution was sterilized at 120° C. and the temperature of the sterile media was brought to 30° C. Then, 15 liters of a sterile 30% solution of dextrose and 10 liters of a bottoms broth of a culture of *Micrococcus caseolyticus* (I. 194) was introduced therein. The culture broth was allowed to ferment for 24 hours at 30° C. while agitating and passing in sterile air, while maintaining the pH constant for the first ten hours. After 24 hours, 1050 liters of raw fermentation broth was recovered.

EXTRACTION OF THE ENZYME

The bacteria contained in 5000 liters of culture broth prepared as above was separated by centrifuging in an Alfa Laval centrifuge type LX. 4770 liters of a limpid centrifugate was recovered.

2670 kg of ammonium sulfate was added to this obtained centrifugate and the media was agitated for 30 minutes, followed by addition of 1.2 kg of Hyflo-supercel. The treated centrifugate was then allowed to stand for 24 hours and the supernatant was separated. The insoluble fraction obtained above was introduced into 330 liters of a calcium chloride solution, agitated for 15 minutes and then filtered. 390 liters of solution was recovered and concentrated by ultrafiltration. After 12 hours, 50 liters of a concentrated solution of enzymes was obtained analysing 50,500 Units/cm$^3$. This concentrated solution of enzymes was then separated into flasks of 24 cm$^3$ volume and lyophilized.

The following examples are illustrative of the practice of the invention without being limitative.

EXAMPLE 1

Production of Carrés de l'Est from pasteurized milk 2000 liters of whole milk containing 36 gm/l of fats (cooled to +4° C.) were treated with lactic ferments and molds. The lactic ferment was C$_5$ of Roger *Penicillium Candidum* lyophilized, utilizing 5 doses for the 2000 liters, each dose containing $2 \times 10^9$ spores. The molding innoculum was 1% of mesophiles Carlin Marshall on Marstar media. Calcium chloride was added to the ferment which was then divided into 20 shallow pans of 100 liters each. Maturation was effected at +35° C. for 2 hours. Then 9000 Units per shallow pan of extracted enzymes of *Micrococcus caseolyticus* was added to the 100 liters contained in each shallow pan, fifteen minutes before treating with rennet. Then, 18 ml of rennet was added into each shallow pan. Coagulation occurred after 15 minutes. After 30 minutes of hardening, the coagulate was cut into $2 \times 2 \times 3$ cm pieces. This was followed by 3 successive mashings of the contents of all the shallow pans with a period of rest of 6 minutes between each mashing. A part of the serum exuded after coagulation was discarded acidity of the serum 42° Dornic), then the coagulum was molded and allowed to drain. The first turning was made after draining, a second turning was made 15 minutes later, a third turning was made 3 hours after the second turning, and then a fourth turning was made 4 hours after the third (acidity of the serum, 70° D). The cheeses were released from the molds 24 hours after the start of the operation and 960 pieces of Carrés de l'Est (pH of the cheese-4.7, acidity of the serum-115° D) were obtained. The cheeses so produced were saleable and consumeable after 21 days of ripening. They could still be retailed after 39 days of ripening.

These results show that the period of commercialization at retail, which normally is 12 days, can be elongated to 18 days when using the process of the invention.

EXAMPLE 2

Production of Carrés de l'Est from pasteurized milk 2000 liters of whole milk containing 28 gm/l of fats (cooled to +4° C.) were treated with a lactic ferment and molds. The lactic ferment was spores of Penicilluim candidum lyophilized, utilizing in 5 doses for the 2000 liters, each dose containing $2 \times 10^9$ spores. The molding inoculum was 1% of mesophiles Carlin Marshall on Marstar media. Calcium chloride was added to the ferment which was then poured into 20 shallow pans of 100 liters each. Maturation was effected at +35° C. for 2 hours. Next an enzyme addition was made to the 100 liters contained in each of 4 shallow pans, respectively at doses of 9,000, 10,000, 11,000, and 12,000 Units of extracted enzyme of Micrococcus caseolyticus (No. I 194), fifteen minutes before treating with rennet. Then, 18 ml of rennet was added to the contents of each of the 20 shallow pans (4 treated with extracted enzyme and 16 non-treated serving as controls). Coagulation occurred in the neighborhood of 20 minutes for the contents of the non-treated shallow pans, in 17 minutes for the contents of the shallow pan treated with 9,000 U of enzymes, and in 16 minutes for the contents of the shallow pans treated with 10,000, 11,000, and 12,000, Units of enzymes. The process continued with 3 successive mashings of the contents of all the shallow pans with a period of rest of six minutes between each mashing. A part of the serum exuded after coagulation was discarded, then the coagulum was molded and allowed to drain. The first turning of the cheeses was made after draining, then a second turning was made 15 minutes after the first. A third turning was made three hours after the end of the second and finally a fourth turning was made four hours after the third. The acidity of the serum was 65° Dornic (°D) for the non-treated cheeses serving as controls, 64° D for the cheeses treated by 9000 U of enzyme, 65° D for the cheeses treated by 10,000 U of enzymes, 70° D for the cheeses treated by 11,000 U of enzymes, and 70° D for the cheeses treated by 12,000 U of enzymes. The cheeses were then released from the molds 24 hours after the start of the operation. 960 pieces of Carrés de l'Est were obtained. The pH of the control cheeses and the cheeses treated with four levels of enzymes on Day +1 is given in the following Table I

TABLE I

| | pH of cheeses | | | |
|---|---|---|---|---|
| Control | 9,000 U | 10,000 U | 11,000 U | 12,000 U |
| 4.80 | 4.90 | 4.90 | 4.90 | 4.90 |

It was only toward the 25 days of ripening that the control cheeses had a texture analogous to that of the treated cheeses after 21 days of ripening.

The treated cheeses were still perfectly consumeable after 39 days of ripening whereas starting from the 31st day the control cheeses were proteolyzed in excess and had an ammonia flavor.

EXAMPLE 3

Production of Carrés de l'Est 2100 liters of whole mile containing 36 gm/l of fats (cooled to +4° C.) were treated with a lactic ferment and molds (spores of Penicillium Candidum lyophilized, 5 doses, 1% of of mesophiles Carlin Marshall on Marstar media). Calcium chloride was then added to the ferment, which was then poured into 21 shallow pans of 100 liters each. Maturation was effected at 35° C. for 2 hours. Next an enzyme addition was made to the 100 liters contained in each 9 shallow pans (called treated) respectively at doses of 7,000, 8,000, 9,000, 10,000, 11,000, 12,000, 13,000, 14,000, and 15,000 Units per shallow pan of extracted enzymes of Micrococcus caseolyticus (No. I. 194), fifteen minutes before treating with rennet. Then, 20 ml of rennet was added to the contents of the 21 shallow pans (9 treated and 12 non-treated). Coagulation occurred in 15 minutes for the contents of the non-treated shallow pans and in 12 to 15 minutes for the contents of the treated shallow pans (more rapidly for the contents of the shallow pan treated with 15,000 Units of enzymes per 100 liters). The process continued with 3 successive mashings of the contents of all the shallow pans with a period of rest of six minutes between each mashing. A part of the serum exuded after coagulation was discarded. Next, the coagulum was molded and allowed to drain. A first turning of the cheese was made after draining, then a second turning was made 15 minutes after the end of the first. A third turning was made three hours after the end of the second and finally a fourth turning was made four hours after the end of the third. After the fourth turning, the acidity of the serum was 65° D for the control or non-treated cheeses, 55° D for the cheeses treated by 7,000, 8,000, and 9,000 U of enzymes, and 58° D for the cheeses treated by 10,000, 11,000, 12,000, 13,000, 14,000, and 15,000 U of enzymes. The cheeses were then released from the molds 24 hours after the start of the operation. 1008 pieces of Carrés de l'Est were obtained. The pH of the control cheeses and the treated cheeses on Day +1 and Day +4 is given in the following Table II.

TABLE II

| | | pH of Cheeses | | | | | | | | |
|---|---|---|---|---|---|---|---|---|---|---|
| | | Treated by X 1000 U of enzymes | | | | | | | | |
| Time | Controls | 7 | 8 | 9 | 10 | 11 | 12 | 13 | 14 | 15 |
| Day +1 | 4.87 | 4.88 | 4.85 | 4.87 | 4.86 | 4.81 | 4.83 | 4.82 | 4.80 | 4.75 |
| Day +4 | 4.60 | 4.59 | 4.63 | 4.64 | 4.68 | 4.65 | 4.63 | 4.67 | 4.68 | 4.67 |

After a ripening period of 21 days, the control cheese and the trated cheeses were taste tested. In each case, the aspect of this taste were noted. The results of this taste testing are given in the following Table III.

TABLE III

| Cheese | Aspect and Taste after 21 days of ripening |
|---|---|
| Controls | White and solid paste slighty proteolysed |
| Treated | |
| 7000 U | onctuous, slight taste of proteolysis |
| 8000 U | onctuous, slightly fluid beneath the crust |
| 9000 U | rather solid and homogenous paste lactic taste |
| 10,000 U | homogenous paste, flat taste |
| 11,000 U | slightly fluid beneath the crust, slight taste of proteolysis |
| 12,000 U | onctuous-fluid beneath the crust, acid taste |
| 13,000 U | very fluid |
| 14,000 U | fluid beneath the crust, acid taste |
| 15,000 U | very fluid |

The results obtained showed that the ripening of treated cheeses is more rapid than the ripening of the control cheeses. All together, the proteolysis is very rapid for the cheeses treated with an increased amount of enzymes.

The preceeding specific embodiments are illustrative of the practice of the invention. It is to be understood however, that other expedients known to those skilled in the art or disclosed herein, may be employed without departing from the spirit of the invention or the scope of the appended claims.

We claim:

1. A process for improving the cheese capacity of milk used in the preparation of a soft paste cheese having a moldy crust and having a dried extract weight of 30% to 50% of the soft paste cheese weight intended to be ripened comprising adding to the milk before or during rennet treatment, during the course of the preparation of the said soft paste cheese, 50 to 190 U/liter of milk of an enzyme extracted from a culture of *Micrococcus caseolyticus*.

2. The process of claim 1 wherein said *Micrococcus caseolyticus* is the strain deposited in the Pasteur Institute in Paris under No. I, 194.

3. The process of claim 1 wherein the amount of said enzyme is between 70 and 150 U/liter of milk.

4. The process of claim 1 wherein the addition of said enzyme is made 15 to 20 minutes before the rennet treatment where said rennet treatment is made at a temperature of about 35° C.

5. The process of claim 1 wherein the addition of said enzyme is made at least 40 minutes before the rennet treatment where said rennet treatment is made at a temperature of 30° to 32° C.

6. The process of claim 1 wherein the addition of said enzyme is made to the milk in the prematuration tank or storage tank.

7. The process of claim 1 in the case where the milk has undergone a pasteurization or a thermization before starting cheese making, the enzyme is diluted into some sterile milk the day before the cheese making then kept at room temperature and then poured into the cheese making tank at the start of filling the same.

8. The process of claim 1 wherein said enzyme is added to said milk during stirring.

9. The soft paste cheeses produced by the process of claim 1.

* * * * *